United States Patent
Huang et al.

(10) Patent No.: US 12,419,837 B2
(45) Date of Patent: Sep. 23, 2025

(54) LIPOSOMAL COMPOSITION CONTAINING MILD ACIDIC ACTIVE AGENT

(71) Applicants: TAIWAN LIPOSOME COMPANY, LTD., Taipei (TW); TLC BIOPHARMACEUTICALS, INC., South San Francisco, CA (US)

(72) Inventors: Ke-Ming Huang, Taipei (TW); He-Ru Chen, Taipei (TW); Keelung Hong, South San Francisco, CA (US)

(73) Assignees: TAIWAN LIPOSOME CO., LTD., Taipei (TW); TLC BIOPHARMACEUTICALS, INC., South San Francisco, CA (US)

(*) Notice: Subject to any disclaimer, the term of this patent is extended or adjusted under 35 U.S.C. 154(b) by 836 days.

(21) Appl. No.: 17/393,949

(22) Filed: Aug. 4, 2021

(65) Prior Publication Data
US 2021/0393525 A1 Dec. 23, 2021

Related U.S. Application Data

(63) Continuation of application No. 16/320,851, filed as application No. PCT/US2017/045939 on Aug. 8, 2017, now abandoned.

(60) Provisional application No. 62/375,698, filed on Aug. 16, 2016, provisional application No. 62/372,096, filed on Aug. 8, 2016.

(51) Int. Cl.
*A61K 9/127* (2025.01)
*A61K 9/1271* (2025.01)
*A61K 31/5575* (2006.01)
*A61K 47/12* (2006.01)

(52) U.S. Cl.
CPC ........ *A61K 9/1271* (2013.01); *A61K 31/5575* (2013.01); *A61K 47/12* (2013.01)

(58) Field of Classification Search
None
See application file for complete search history.

(56) References Cited

U.S. PATENT DOCUMENTS

| | | | | |
|---|---|---|---|---|
| 5,034,228 A | * | 7/1991 | Meybeck | A61K 9/127 436/829 |
| 5,925,375 A | * | 7/1999 | Lenk | A61K 9/127 514/573 |
| 5,939,096 A | * | 8/1999 | Clerc | A61K 9/1278 424/450 |
| 2005/0070481 A1 | * | 3/2005 | Fujii | A61P 3/02 514/474 |

(Continued)

*Primary Examiner* — Dominic Lazaro
(74) *Attorney, Agent, or Firm* — LEASON ELLIS LLP

(57) ABSTRACT

Provided is a method for preparing a liposomal composition. The method comprises the step of contacting a liposome solution with a mild acidic agent for a limited time. The liposome solution comprises a weak acid salt encapsulated within an aqueous interior space separated from the aqueous medium by a membrane comprised of a lipid mixture containing one or more lipids and a hydrophilic polymer conjugated lipid at a molar percentage of less than 3% based on the total amount of the lipid mixture. The time for encapsulating the agent to a desired amount at a predetermined ratio to lipids is dramatically reduced even under a condition without elevating the temperature to above ambient environment.

15 Claims, 2 Drawing Sheets

(56) References Cited

U.S. PATENT DOCUMENTS

2014/0105968 A1* 4/2014 Takeuchi ............ A61K 9/1271
424/450
2017/0027869 A1* 2/2017 Barenholz .......... A61K 47/6951
2017/0239182 A1* 8/2017 Hayes .................... A61K 9/127

* cited by examiner

LIPOSOMAL COMPOSITION CONTAINING MILD ACIDIC ACTIVE AGENT

BACKGROUND

1. Technical Field

The present disclosure relates to a delivery vehicle, kit or method for preparing liposomes encapsulating a therapeutic agent, particularly a weak acid drug.

2. Description of Related Art

There have been many approaches to improving the stability or other properties in association with therapeutic functions of a weak acid drug. Weak acid drugs, such as prostaglandins (PGs), have disadvantages for pharmaceutical use. For example, Edex® is a sterile, pyrogen-free powder containing in alpha-cyclodextrin inclusion complex, also known as an alpha-cyclodextrin form of prostaglandin $E_1$ ($PGE_1$-CD). It is freely soluble in water and practically insoluble in ethanol, ethyl acetate and ether. After reconstitution, the active ingredient, alprostadil, immediately dissociates from the α-cyclodextrin inclusion complex. However, due to the short half life in human body of $PGE_1$ (about 30 seconds) and its serious side effect when being overdosed, a high frequency of administrating limited dose remains necessary in treatment of $PGE_1$-CD. Other pharmaceutical preparations are in the form of suspension in which $PGE_1$ is dissolved in lipid microspheres, which is an oil-in-water type emulsion. However, the stability on shelf or in plasma of such preparations is not sufficient (U.S. Pat. No. 4,684,633).

In one aspect, to improve the inconvenient treatment of the conventional weak acid drug preparations, liposomal formulations are applied to deliver weak acid drugs, such as PG. U.S. Patent Publication no. US20020182248 disclosed liposomal dispersion by using a specified lipid, sphingolipid. However, this conventional liposomal dispersion is prepared by passive loading with a non-ensured encapsulation efficiency of PG. Unentrapped PG could lead to overdose problems during its administration to a subject.

In another aspect, to prevent aggregation of liposomes in blood and to avoid being captured by reticuloendothelial system (RES), the surface of liposome is coated with poly (ethylene glycol)(PEG). PEG-derivatized liposomes, known as stealth liposomes, that contain entrapped doxorubicin show enhanced therapeutic efficacy in preclinical studies due to increased tumor tissue drug level achieved after treatment with long-circulating liposomes (U.S. Pat. Nos. 5,013,556, 5,676,971). However, little is proven to be applicable for loading or encapsulating weak acid drugs in PEG-derivatized liposomes with a prompt procedure under ambient temperature for ease of clinical use. Moreover, there is still a need of liposome dispersion having a high efficiency in loading weak acid drugs, particularly PG, into PEG-derivatized liposomes to avoid problems of overdose caused by free drug or of degradation of drug in aqueous dispersion.

In yet another aspect, to stably encapsulate a chemical entity in liposomes at a higher efficiency, U.S. Pat. No. 5,939,096 utilizes a proton shuttle mechanism involving the salt of a chemical entity to generate a higher inside/lower outside pH gradient and to achieve a cation-promoted precipitation or low permeability across the liposome transmembrane barrier.

However, based on the previous technique for loading a weak acid drug into liposomes or stealth liposomes in conjunction with an experimental data (FIG. 1) conducted by the Applicants, it demonstrates that stealth liposomes possess poor encapsulation efficiency at an ambient temperature (25° C.) and require a heating step to increase permeability of prostaglandins. The loading procedure requires elevating the temperature above the transitional temperature of the liposomes, typically higher than 60° C., which is generally higher than an ambient temperature. The elevated temperature accelerates the degradation of labile drug, such as prostaglandins, when being exposed to an aqueous environment, and thus hampers the stability of the composition in long term storage.

To overcome the shortcomings, the present disclosure provides a method and a kit for preparing a liposomal composition containing polyethylene glycol-derivatized liposomes adapted for obtaining a higher encapsulation efficiency at an ambient temperature and exerting a desired pharmacokinetics for sustained releasing a weak acid drug, and preferably an enhanced stability in shelf storage to mitigate or obviate the aforementioned problems.

SUMMARY

The present disclosure is based on the discovery that a reduced amount of hydrophilic polymer conjugated lipid in a mixture of lipids for forming liposomes with a gradient of a weak acid salt is useful for loading and retaining an acidic compound in liposomes. Accordingly, the present disclosure provides methods, kits, or compositions for delivering a variety of acidic compounds useful in the diagnosis, prognosis, treatment or prevention of an illness, disease, condition or symptom in a subject.

In one aspect of the present disclosure, provided is a delivery vehicle, said delivery vehicle comprising a liposome in an aqueous medium,
wherein the liposome having an interior space, and
the interior space:
1) is aqueous,
2) is separated from the aqueous medium by a membrane comprised of a lipid mixture, wherein the lipid mixture contains one or more lipids and a hydrophilic polymer conjugated lipid at a molar percentage of less than 3% based on the total amount of the lipid mixture; and
3) contains a weak acid salt.

In another aspect of the present disclosure, provided is a method of preparing a liposomal composition, which comprises:
contacting, in an aqueous medium, a liposome comprising a weak acid salt encapsulated within an aqueous interior space separated from the aqueous medium by a membrane comprised of a lipid mixture;
with a mild acidic agent for a sufficient time, whereby the mild acidic agent becomes encapsulated within the liposome;
wherein the weak acid salt has a cation pairing with the mild acidic agent, and the lipid mixture contains one or more lipids and a hydrophilic polymer conjugated lipid at a molar percentage of less than 3% based on the total amount of the lipid mixture.

In a group of embodiments, the hydrophilic polymer conjugated lipid is polyethylene glycol-derived lipid at a molar percentage ranging from 0.1% to 3% based on the total amount of the lipid mixture; preferably from 0.5% to 3%; and more preferably, from 0.5% to 1%.

In a group of embodiments, the liposome further comprises a polyprotic acid encapsulated within the liposome in the aqueous interior space, whereby the polyprotic acid provides for excellent retention of the entrapped prostaglandin in the liposome. Generally, the polyprotic acid is a natural acid or a synthetic biocompatible acid. Preferably, the polyprotic acid is an organic tribasic acid. In one embodiment, the polyprotic acid is selected from the group consisting of citric acid, succinic acid, tartaric acid or a combination thereof.

In a group of embodiments, the contacting in an aqueous medium, a liposome with a mild acidic agent is performed under a condition of being at an ambient temperature for the time sufficient for the mild acidic agent becoming encapsulated within the liposome.

In yet another aspect of the present disclosure, provided is a kit for preparing a liposomal composition containing a mild acidic agent, which comprises:
one container accommodating a lyophilized cake, wherein the lyophilized cake contains a mild acidic agent; and
another container accommodating a liposomal solution, wherein the liposome solution contains a liposome in an aqueous medium,
wherein the liposome includes a weak acid salt encapsulated within an aqueous interior space separated from the aqueous medium by a membrane comprised of a lipid mixture, wherein the lipid mixture contains one or more lipids and a hydrophilic polymer conjugated lipid at a molar percentage less than 3% based on the total amount of the lipid mixture.

In one general embodiment, the mild acidic agent is a physiologically active lipid derived from fatty acid. Particularly, the mild acidic agent is arachidonic acid metabolite, such as a prostaglandin (PG) including prostacyclin or a thromboxane, which is a hormone-like substance that participates in a wide range of body functions such as the contraction and relaxation of smooth muscle, the dilation and constriction of blood vessels, control of blood pressure, inhibition of platelet aggregation and modulation of inflammation. Prostaglandins have been developed as pharmaceuticals or therapeutic compound in the treatment of hypertension, thrombosis, asthma, and gastric and intestinal ulcers, for indication of labor and abortion in pregnant mammals, and for prophylaxis of arteriosclerosis.

In one general embodiment, the mild acidic agent is prostaglandin $A_1$ ($PGA_1$), prostaglandin $A_2$ ($PGA_2$), prostaglandin $E_1$ ($PGE_1$), prostaglandin $E_2$ ($PGE_2$), prostaglandin $F_1\alpha$ ($PGF_1\alpha$) or prostaglandin $F_2\alpha$ ($PGF_2\alpha$).

In one preferred embodiment, the mild acidic agent in accordance with the present disclosure is Prostaglandin $E_1$ ($PGE_1$) (also known as alprostadil) or its derivative, such as but not limited to 6-keto-Prostaglandin $E_1$, 15-keto-Prostaglandin $E_1$, 13,14-dihydro-15-keto Prostaglandin $E_1$, or 16,16-dimethyl-6-keto prostaglandin $E_1$, which is suitable for the treatment for intermittent claudication patients. For intermittent claudication patients, alprostadil can increase their peripheral blood flow and permeability of blood vessel, and inhibit platelet aggregation. $PGE_1$ can relieve patients from pain caused by insufficient blood flow in peripheral circulation. However, the conventional treatment with $PGE_1$-CD (alpha-cyclodextrin form) is inconvenience for patients in a regimen of BID (twice a day) for weeks. In another aspects, for half life of $PGE_1$ is short (varying between about 30 seconds and 10 minutes) in human body and its side effect could be serious when overdosed (it reduces blood pressure), high frequency for limited dose is necessary in $PGE_1$-CD treatment.

For improving this inconvenience treatment of conventional prostaglandins, the present disclosure provides a delivery vehicle, a kit or a method for preparing a liposomal composition containing prostaglandin, particularly a liposomal $PGE_1$ formulation wherein $PGE_1$ is encapsulated within liposomes. One of the benefits for liposomal formulations is to allow $PGE_1$ gradually released from liposomes in the liposomal composition for treatments in subject diseases or symptoms at extended intervals. Also, since only free form $PGE_1$ will cause the side effect but not liposomal form, the dosage of liposomal $PGE_1$ can be increased without gaining serious side effect problem. The delivery vehicles, kits and methods according to the present disclosure provide a more friendly and continence product for patient usage.

One of the objectives of the present disclosure is to establish a ready-to-use liposomal composition containing the mild acidic agent such as $PGE_1$ in a form of two-vial kit. To achieve better clinical usage, higher encapsulation efficiency after a short duration and remote loading at ambient temperature are required. Higher encapsulation efficiency reduces free form of the agent which could cause undesired side effect while overdosed. On the other hand, more retained agent after in vitro release, which represents sustained release properties, is also required. Besides, for such objective of the present disclosure, the kit should be stable in storage for at least one year in 4° C. and show efficacy in animal models. Based on those requirements, the parameters of the subject delivery vehicle, kit and method are modified to achieve the requirements.

Other objectives, advantages and novel features of the disclosure will become more apparent from the following detailed description when taken in conjunction with the accompanying drawings.

DETAILED DESCRIPTION OF THE PREFERRED EMBODIMENTS

I. Definition

Figure 1:
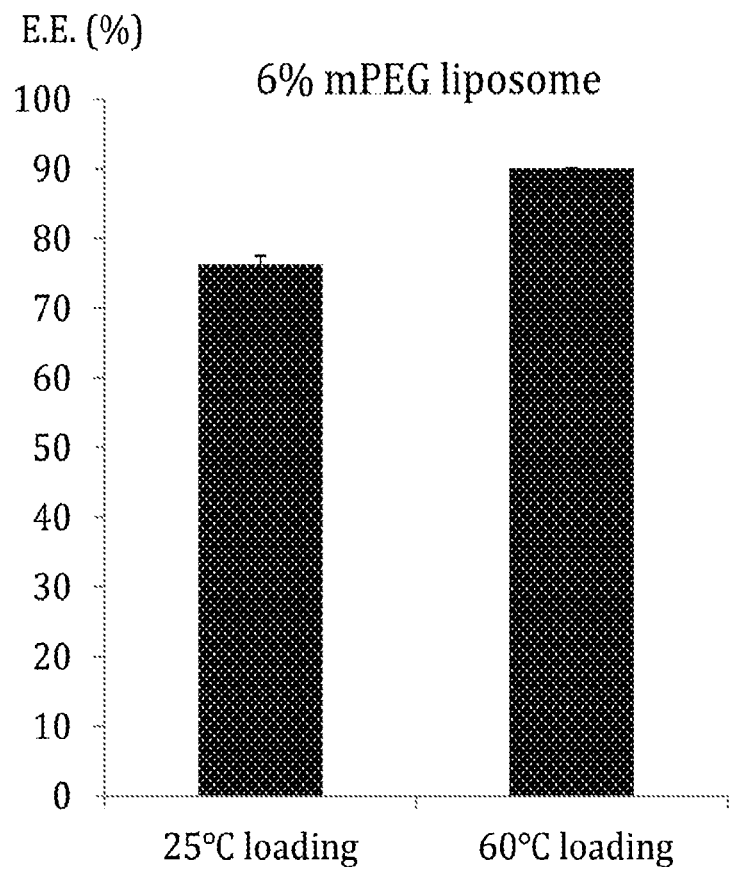
FIG. 1 illustrating a diagram of comparison between the encapsulation efficiency of prostaglandin into liposome with conventionally workable amounts of polyethylene glycol-derived lipid, 6%, under conditions of ambient temperature and elevated temperature.

As employed above and throughout the disclosure, the following terms, unless otherwise indicated, shall be understood to have the following meanings.

As used herein, the singular forms "a", "an" and "the" include the plural reference unless the context clearly indicates otherwise.

All numbers herein may be understood as modified by "about."

Liposome

The term "liposome" as used herein is usually characterized by having an aqueous interior space sequestered from an outer medium by a membrane of one or more bilayers forming a vesicle. Bilayer membranes of liposomes are typically formed by lipids, i.e. amphiphilic molecules of synthetic or natural origin that comprise spatially separated hydrophobic and hydrophilic domains. Preferably, liposomes, in the practice of the present disclosure, include small unilamellar liposome (SUV), large unilamellar liposome (LUV), i.e., a unilamellar liposome with a diameter of greater than 50 nm and multilamellar liposomes (MLVs) having more than one lipid bilayer.

In general, liposomes are composed of a lipid mixture including one or more lipids. Examples of lipids includes, but not limited to, (i) neutral lipid, e.g. cholesterol, ceramide, diacylglycerol, acyl(poly ethers) or alkylpoly (ethers); (ii) neutral phospholipid, e.g., diacylphosphatidylcholines, sphingomyelins, and diacylphosphatidylethanolamines, (iii) anionic lipid, e.g., diacylphophatidylserine, diacylphosphatidylglycrol, diacylphosphatidate, cardiolipin, dacylphophatidylinositol, diacylglycerolhemisuccinate, diacylglycerolhemiglutarate, and the like; and (v) cationic lipid, e.g., dimethyldioctadecylammonium bormide (DDAB), 1, 2,-diacyl-3-trimethylammonium propane (DOTAP), and 1,2-diacyl-sn-glycero-3-ethylphosphocholine.

In a typical case of the hydrophilic polymer derivatized liposome, the liposome is composed of a mixture of at least one phospholipid and a neutral lipid, and a hydrophilic polymer conjugated lipid. Examples of the phospholipid used in the present disclosure include, but are not limited to, phosphatidylcholine (PC), phosphatidylglycerol (PG), phosphatidylethanolamine (PE), phosphatidylserine (PS), phosphatidic acid (PA), phosphatidylinositol (PI), egg phosphatidylcholine (EPC), egg phosphatidylglycerol (EPG), egg phosphatidylethanolamine (EPE), egg phosphatidylserine (EPS), egg phosphatidic acid (EPA), egg phosphatidylinositol (EPI), soy phosphatidylcholine (SPC), soy phosphatidylglycerol (SPG), soy phosphatidylethanolamine (SPE), soy phosphatidylserine (SPS), soy phosphatidic acid (SPA), soy phosphatidylinositol (SPI), dipalmitoylphosphatidylcholine (DPPC), 1,2-dioleoyl-sn-glycero-3-phosphatidylcholine (DOPC), dimyristoylphosphatidylcholine (DMPC), dipalmitoylphosphatidylglycerol (DPPG), dioleoylphosphatidylglycerol (DOPG), dimyristoylphosphatidylglycerol (DMPG), hexadecylphosphocholine (HEPC), hydrogenated soy phosphatidylcholine (HSPC), distearoylphosphatidylcholine (DSPC), distearoylphosphatidylglycerol (DSPG), dioleoylphosphati dylethanolamine (DOPE), palmitoylstearoylphosphatidylcholine (PSPC), palmitoylstearoylphosphatidylglycerol (PSPG), monooleoylphosphatidylethanolamine (MOPE), 1-palmitoyl-2-oleoyl-sn-glycero-3-phosphatidylcholine (POPC), distearoylphosphatidylethanolamine (DSPE), dipalmitoylphosphatidylserine (DPPS), 1,2-dioleoyl-sn-glycero-3-phosphatidylserine (DOPS), dimyristoylphosphatidylserine (DMPS), distearoylphosphatidylserine (DSPS), dipalmitoylphosphatidic acid (DPPA), 1,2-dioleoyl-sn-glycero-3-phosphatidic acid (DOPA), dimyristoylphosphatidic acid (DMPA), distearoylphosphatidic acid (DSPA), dipalmitoylphosphatidylinositol (DPPI), 1,2-dioleoyl-sn-glycero-3-phosphatidylinositol (DOPI), dimyristoylphosphatidylinositol (DMPI), distearoylphosphatidylinositol (DSPI), and a mixture thereof.

Hydrophilic Polymer Conjugated Lipid

The term "hydrophilic polymer conjugated lipid" refers to hydrophilic polymer with a long chain of highly hydrated flexible neutral polymer attached to a lipid molecule. Examples of the hydrophilic polymer includes, but not limited to, polyethylene glycol (PEG) with a molecular weight about 2,000 to about 5,000 daltons, methoxy PEG (mPEG), ganglioside $GM_1$, polysialic acid, polyglycolic acid, apolyacticpolyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose and synthetic polymers. Examples of the lipid molecule includes, but not limited to (i) neutral lipid, e.g. cholesterol, ceramide, diacylglycerol, acyl(poly ethers) or alkylpoly (ethers); (ii) neutral phospholipid, e.g., diacylphosphatidylcholines, sphingomyelins, and diacylphosphatidylethanolamines, (iii) anionic lipid, e.g., diacylphophatidylserine, diacylphosphatidylglycrol, diacylphosphatidate, cardiolipin, dacylphophatidylinositol, diacylglycerolhemisuccinate, diacylglycerolhemiglutarate, and the like; and (v) cationic lipid, e.g., dimethyldioctadecylammonium bormide (DDAB), 1, 2,-diacyl-3-trimethylammonium propane (DOTAP), and 1,2-diacyl-sn-glycero-3-ethylphosphocholine.

In one group of embodiment, the hydrophilic polymer conjugated lipid is the polyethylene glycol-derived lipid, which includes, but not limited to: DSPE-PEG, wherein the molecular weight of PEG is about 2,000 daltons (hereafter $DSPE-PEG_{2000}$).

Encapsulation

The term "encapsulated" or "entrapped" compound, substance or a therapeutic agent refers to a compound, substance or a therapeutic agent is associated with the liposome or sequestered, at least in part, in the internal compartment of liposome. The term "encapsulation efficiency" refers to the ratio of an amount of the liposomal form of drug to a sum of free form drug and liposomal form of drug. In one group of embodiments, the encapsulation efficiency is calculated based on the amount of the entity encapsulated in the liposome divided by a sum of an amount of the entity not encapsulated in the liposome and the entity encapsulated in the liposome, which is determined using various methods as known in the art.

Weak Acid Salt

The term "weak acid salt" refers to the conjugate base of the weak acid. As used herein, weak acid salt refers to both the conjugate base of the weak acid and to any accompanying counterion. Preferably, a weak acid salt for use in the present disclosure is water soluble at high concentrations. The counterion or cation should be practically lipid-membrane impermeable (having permeability coefficient, P, of less than about $10^{-12}$ to $10^{-11}$ cm/s). The counterion may be monovalent or multivalent. Exemplary weak acid for use in the present disclosure include carboxylic acids such as formic acid, acetic acid, propanoic acid, butanoic acid, pentanoic acid, and substituted derivatives thereof. Exemplary cation for use in the present disclosure include sodium, potassium, ammonium and calcium. Preferably, calcium is used as cation while prostaglandin is selected as the mild acidic agent in accordance with the present disclosure.

Polyprotic Acid

The term "polyprotic acid" refers to weak organic polybasic acid. Exemplary polyprotic acid for use in the present disclosure include citric acid, tartaric acid, succinic acid, adipic acid and aconitic acid, typically at 1 to 20 mM concentration.

Preferably, a polyprotic acid for use in the present disclosure is citric acid at a concentration less than 3 mM; more preferably, less than 2.5 mM; and most preferably less than 2.3 mM. In a particular embodiment, the concentration of citric acid is from 1.5 to 2.5 mM.

Mild Acidic Agent

The term "mild acidic agent" as used herein refers to a compound intended for loading into liposomes, and which also contains at least one carboxy group and is amphipathic. The pKa of the agent is typically less than about 5. In a particular embodiment, the pKa of the agent is about 4.85.

The agent may also contain one or more functional groups in addition to the carboxy function, although the presence of such functional group should not significantly alter the acidity of the agent from that of its non-functionalized counterpart. The agent refers to both the compound in its protonated form to any salt forms thereof. A salt of the agent may be accompanied by any pharmaceutically acceptable counterion.

The term "amphipathic" is used herein to denote a compound containing both polar and nonpolar domains and thus having the ability to permeate normally nonpermeable membrane under suitable conditions.

The term "amphipathic" is used herein to denote a molecule having both hydrophobic (nonpolar) and hydrophilic (polar) groups, and being characterized by any one of the following: pKa: it has a pKa above 3.0, preferably above 3.5, more preferably, in the range between about 3.5 and about 6.5; Partition coefficient: in an n-octanol/buffer (aqueous phase) system having a pH of 7.0, it has a log D in the range between about −3 and about 2.5.

Lyophilized Cake

The term "lyophilized cake" refers to a freeze-drying product containing a mild acidic agent, which processes desirable characteristics including maintenance of the characteristics of the original dosage form upon reconstitution, including solution properties; and particle-size distribution of suspensions; and isotonicity upon reconstitution.

II. Preparation of Liposome Solution for Loading

The present disclosure provides a liposome solution having liposomes with a gradient of weak acid salt for loading a mild acidic agent across the gradient. General methods for preparing the liposome solution is described as below.

A. Liposome Formation

Liposomes with a weak acid salt entrapped within an aqueous interior space, which is suitable for forming the liposome solution in accordance with the present disclosure, may be prepared by a variety of techniques. Examples of methods suitable for making liposomes of the present disclosure include solvent injection, reverse phase evaporation, sonication, microfluidisation, detergent dialysis, ether injection, and dehydration/rehydration. In a typical procedure, a lipid mixture is dissolved in ethanol and injected into a hydration buffer containing a weak acid salt, such as sodium or calcium acetate.

Typically, the membrane of the liposome is composed of a lipid mixture, wherein the lipid mixture includes a phospholipid or a mixture of at least one phospholipid and neutral lipid, and a hydrophilic polymer conjugated lipid. In a preferable embodiment, the lipid mixture is composed of one or more phospholipid and cholesterol and a hydrophilic polymer conjugated lipid, wherein the hydrophilic polymer conjugated lipid is DSPE-mPEG at a molar percentage of less than 3% based on the total amount of the lipid mixture. In a group of embodiments, the molar percentage of cholesterol ranges from 10% to 40% based on the total amount of the lipid mixture. In one group of embodiments, the phospholipid is selected from DSPC, DMPC, DPPC and DOPC. In another group of embodiments, the amount of phospholipid, cholesterol and DSPE-mPEG is at a molar ratio of 3:2:0.045.

The hydration buffer suitable for the present disclosure contains sodium acetate, potassium acetate or calcium acetate. In one group of embodiments, the hydration buffer contains sodium acetate and is preferably at a concentration of at least 100 mM; and typically, between 100 mM and 800 mM; preferably between 200 mM and 800 mM; and most preferably between 400 mM and 800 mM. In another group of embodiments, the hydration buffer contains calcium acetate at a concentration preferably between 200 mM and 400 mM; and more preferably 250 mM and 350 mM. The hydration buffer is adjusted by addition of acid or base at a pH between 4.0 and 9.0, preferably between 7.5 and 8.5, and most preferably of 8.2. In an alternative embodiment, while the hydration buffer further contains a polyprotic acid, such as citric acid, the preferable pH is adjusted to 6.5 and its retained $PGE_1$ could be relatively maintained after in vitro release assay in comparison to that without the polyprotic acid.

For the mild acidic agent as well as the weak acid being allowed to distribute between inner and outer compartments, acting as an inside to outside proton shuttle, retention of the mild acidic agent may alter among a variety of components in the interior space of the liposome. To modulate the retention of the mild acidic agent, the hydration buffer is adjusted to contain a polyprotic acid. However, addition of the polyprotic acid into the hydration buffer decrease the pH of the aqueous interior space of the liposomes causes an undesirably reduction in the encapsulation efficiency. In a preferable embodiment, the hydration buffer contains a polyprotic acid at a concentration less than 50 mM, preferably less than 10 mM, more preferably between 0.01 mM and 5 mM, much more preferably between 0.1 mM and 3 mM, and most preferably between 1.5 mM and 2.5 mM.

The size of the liposomes can be controlled by controlling the pore size of membranes used for low pressure extrusion or the pressure and number of passes utilized in microfluidisation or any other suitable method. The liposomes in accordance with the present disclosure have a mean diameter of about 30 nm to about 200 nm, more preferably about 50 nm to about 150 nm.

B. Establishing Gradient of Weak Acid Salt

After sizing, the exterior hydration buffer of the liposomes is processed to form a higher inside concentration gradient of weak acid salt, e.q. sodium acetate. This could be done by a variety of techniques, e.g., by (a) dilution of an aqueous medium, (b) dialysis against an aqueous medium, (c) molecular sieve chromatography, or (d) high-speed centrifugation and resuspending of centrifuged liposomes in an aqueous medium, wherein the aqueous medium is suitable for physical condition and pharmaceutical administration.

In a general case, the aqueous medium, alternatively used as exterior buffer, contains a buffer and a solute for maintaining a desired osmolarity and is adjusted pH at a range between 4 and 7, preferably between 4 and 5, and most preferably at 5.5. The exemplary buffer is histidine, MES or the like at a pH 4 to 7 at a concentration at a range of 5 to 50 mM, and preferably 20 mM. The exemplary solute is salt of a strong acid, to form a saline, or mono- or di-sacchride, such as sucrose, glucose, mannitol, lactose or maltose.

III. Preparation of Lyophilized Cake

Lyophilized cake for use in the present disclosure may be prepared by a variety of techniques. Typically, the lyophilization process consists of three stages: freezing, primary drying, and secondary drying. The design of a lyophilized formulation is dependent on the requirements of the active pharmaceutical ingredient (API), herein the mild acidic agent, and intended route of administration. In an alternative embodiment, a stock solution containing the mild acidic agent is applicable to the present disclosure and consists of: an organic solvent, such as tert-Butyl alcohol (TBA); a cryoprotectant; and the mild acidic agent. The stock solution is subjected to the lyophilization process to obtain said lyophilized cake. The exemplary lyophilized cake contains a water content at a range of 1.2% to 1.5% and amounts of the mild acidic agent to cryoprotectant at a ratio of 0.0001:1.0 to 0.01:1.5, preferably, 0.005:1.25, and more preferably, 0.0526:125 by weight. In a particular embodiment, the cryoprotectant is maltose.

IV. Method for Preparing Liposomal Composition Containing a Mild Acidic Agent The hydrophilic polymer-derived liposomes encapsulating the mild acidic agent are prepared by the method according to the present disclosure.

In a typical procedure, a liposomal composition is prepared by contacting a liposome solution in accordance with the present disclosure with a lyophilized cake containing a mild acidic agent at a condition for the mild acidic agent to become encapsulated within the liposome, wherein the condition includes being at an ambient temperature, typically 18° C. to 30° C., for a period of time shorter than 20 minutes. The liposome containing the mild acidic agent which is encapsulated within the aqueous interior space separated from the aqueous medium by the membrane is thus obtained and ready for use in pharmaceutical or other application.

In general, the liposomal composition is obtained by contacting the liposome solution and the lyophilized cake at a predetermined drug to lipid ratio. The drug to lipid ratio hereby refers to ratio of the amount of the mild acidic agent in the lyophilized cake to the amount of lipids in the liposome solution. An exemplary molar ratio of drug to lipid is from 0.001:1 to 0.05:1 Typically, the ratio of $PGE_1$:lipid ranges from 20 µg:5 µmol to 10 µg:20 µmol.

In a group of embodiments, the condition includes, but not limited to a time sufficient for the mild acidic agent to become encapsulated within the liposome at an ambient temperature, the time is a least 5 minutes, for examples, 10 minutes, 60 minutes or 24 hours; and preferably at least 10 minutes. More preferably, the condition includes allowing the mild acidic agent to become encapsulated with the liposome at an ambient temperature, which generally ranges from 18° C. to 30° C.

The resulting liposomal composition has encapsulation efficiency at least 85%; and optionally at least 90%, 95%, or 97%; and preferably 95 to 99%.

The disclosure will now be described in further detail with reference to the following specific, non-limiting examples.

EXAMPLE 1

Process for Preparing Lyophilized Cake

Cryoprotectant was dissolved in hot water (50~60° C.) and then cooled to below 40° C. to form a cryoprotectant solution. Prostaglandin $E_1$ was dissolved in tert-Butyl alcohol (TBA) being pre-warmed to liquefy the solvent at 40° C. and then transferred to and mixed with the cryoprotectant solution to form a prostaglandin solution. The prostaglandin solution was subjected to aseptic filtration and filled into 6R vial, followed by lyophilization to form a lyophilized cake containing $PGE_1$ (hereby also denoted as alprostadil cake). The lyophilization was performed with a shelf lyophilizer under a program with the parameters as listed in the below Table I.

TABLE I

The lyophilization parameters for alprostadil cake

|  | Freeze | Primary drying | Secondary drying | End |
|---|---|---|---|---|
| temperature (° C.) | −40 | −40 | −30 | 30 | 4 |
| duration (min) | 90 | 240 | 3000 | 720 | — |
| pressure (mTorr) | — | — | 100 | 100 | 100 |

EXAMPLE 2

Preparation of Alprostadil Cake with Various Components

To find a suitable formulation for forming the alprostadil cake according to the present disclosure, 52.6 µg $PGE_1$ per vial was proposed for alprostadil cake, 125 mg cryoprotectant was used for our formulation.

As $PGE_1$ was used as API in the formulation, a suitable solvent was needed to dissolve water-insoluble $PGE_1$. $PGE_1$ is soluble in tert-Butyl alcohol (TBA). TBA was selected to dissolve $PGE_1$ to form the prostaglandin solution.

$PGE_1$ undergo dehydration to form prostaglandin $A_1$. In order to increase the shelf life of $PGE_1$, lyophilization was used to reduce the moisture content to a very low level to minimize the degradation. Screening of the candidate formulations were based on results of 40° C. accelerated stability test.

As the content of cryoprotectant and $PGE_1$ per vial was fixed as above, the other lyophilization parameters, such as water content, TBA addition or others were further modulated as described in Table II and investigated as described in the following examples.

TABLE II

Formulation of the alprostadil cake

| Formulation Code | Type of cryoprotectant | Composition per vial: mg (% (w:w)) | | | |
|---|---|---|---|---|---|
| | | $PGE_1$* | TBA | cryoprotectant | water |
| Pc029 | lactose monohydrate | 0.0526 (0.0039) | 13.8 (1.02) | 125 (9.26) | 1211.1 (89.71) |
| Pc030 | lactose monohydrate | 0.0526 (0.0050) | 10.8 (1.02) | 125 (11.90) | 914.2 (87.07) |
| Pc031 | lactose monohydrate | 0.0526 (0.0058) | 9.2 (1.02) | 125 (13.89) | 765.7 (85.08) |
| Pc032 | lactose monohydrate | 0.0526 (0.0070) | 7.7 (1.02) | 125 (16.67) | 617.3 (82.30) |
| Pc033 | lactose monohydrate | 0.0526 (0.0070) | 16.5 (2.19) | 125 (16.67) | 608.5 (81.13) |

TABLE II-continued

Formulation of the alprostadil cake

| Formulation Code | Type of cryoprotectant | Composition per vial: mg (% (w:w)) | | | |
|---|---|---|---|---|---|
| | | $PGE_1$* | TBA | cryoprotectant | water |
| Pc034 | lactose monohydrate | 0.0526 (0.0070) | 27.4 (3.66) | 125 (16.67) | 597.5 (79.67) |
| Pc035 | sucrose | 0.0526 (0.0070) | 7.7 (1.02) | 125 (16.67) | 617.3 (82.30) |
| Pc036 | maltose monohydrate | 0.0526 (0.0070) | 7.7 (1.02) | 125 (16.67) | 617.3 (82.30) |

*52.6 µg instead of 50 µg of $PGE_1$ was used hereby to adjust the final concentration of $PGE_1$ after reconstitution by 5 mL liposome solution to be 10 µg/mL.

EXAMPLE 2A

Effect of Water Content in the Prostaglandin Solution

First, upon the fixed percentage of TBA, the effect of percentage of water before lyophilization was investigated by using the formulations as listed in Table III to form the alprostadil cakes.

TABLE III

Formulations of the prostaglandin solutions with various water content

| Formulation Code | Composition per vial: mg (% (w:w)) | | | |
|---|---|---|---|---|
| | $PGE_1$* | TBA | lactose monohydrate | water |
| Pc029 | 0.0526 (0.0039) | 13.8 (1.02) | 125 (9.26) | 1211.1 (89.71) |
| Pc030 | 0.0526 (0.0050) | 10.8 (1.02) | 125 (11.90) | 914.2 (87.07) |
| Pc031 | 0.0526 (0.0058) | 9.2 (1.02) | 125 (13.89) | 765.7 (85.08) |
| Pc032 | 0.0526 (0.0070) | 7.7 (1.02) | 125 (16.67) | 617.3 (82.30) |

*52.6 µg instead of 50 µg of $PGE_1$ was used hereby to adjust the final concentration of $PGE_1$ after reconstitution by 5 mL liposome solution to be 10 µg/mL As shown in Table IV, all formulations met the criteria of 90% $PGE_1$ remaining after 6 weeks at 40° C., the remaining content decreased as percentage of water in the prostaglandin solution decreased. It demonstrated that reduction of the opportunity of contact of API with water by increasing the inter-space (by increasing the percentage of water) could improve the stability of alprostadil cakes. Furthermore, no significant differences between Formulations Pc029 and Pc030 demonstrated that as inter-space increased to a certain value, API and water was separated at a large enough space. In order to minimize the time of lyophilization, the formulation with the least water content was the favorable candidate. Formulation Pc030 was selected instead of Formulation Pc029.

TABLE IV

Stability of the obtained alprostadil cakes at 40° C. after 6 weeks

| Formulation Code | remaining $PGE_1$ (%) | $PGA_1$ (%) | water content (%) |
|---|---|---|---|
| Pc029 | 95.9 ± 0.5 | 4.0 ± 0.4 | 1.40 ± 0.15 |
| Pc030 | 96.1 ± 0.5 | 4.3 ± 0.0 | 1.34 ± 0.03 |
| Pc031 | 93.6 ± 1.0 | 5.2 ± 0.12 | 1.41 ± 0.04 |

EXAMPLE 2B

Effect of Solvent Content in the Prostaglandin Solution

Second, effect of the content of TBA in the $PGE_1$ solution was investigated by using the formulations as listed in Table V to form the alprostadil cakes.

TABLE V

Formulations of the prostaglandin solutions with various TBA concentrations

| Formulation Code | Composition per vial: mg (% (w:w)) | | | |
|---|---|---|---|---|
| | $PGE_1$ | TBA | lactose monohydrate | water |
| Pc032 | 0.0526 (0.0070) | 7.7 (1.02) | 125 (16.67) | 617.3 (82.30) |
| Pc033 | 0.0526 (0.0070) | 16.5 (2.19) | 125 (16.67) | 608.5 (81.13) |
| Pc034 | 0.0526 (0.0070) | 27.4 (3.66) | 125 (16.67) | 597.5 (79.67) |

As shown in Table VI, increase of the TBA content slowed the degradation of $PGE_1$. It was suggested to be caused from variance of crystallization in freeze step, a loose apparent cake was observed in the group of high TBA content in comparison to a crystal-like in the group of low TBA content, which indicated crystallization varied in the groups with various TBA content. The variance of crystal conditions influenced stability of $PGE_1$ and led to the observed results.

TABLE VI

Stability of the obtained alprostadil cakes at 40° C. after 6 weeks

| Formulation number | remaining $PGE_1$ (%) | $PGA_1$ (%) | water content (%) |
|---|---|---|---|
| Pc032 | 90.7 ± 1.0 | 9.7 ± 1.1 | 1.27 ± 0.02 |
| Pc033 | 95.2 ± 1.1 | 3.6 ± 0.4 | 1.35 ± 0.07 |
| Pc034 | 94.9 ± 2.5 | 5.0 ± 0.8 | 1.36 ± 0.02 |

EXAMPLE 2C

Effect of Cryoprotectant Content in the Prostaglandin Solution

Finally, effect of the different cryoprotectants as identified in Table VII were also investigated by using formulations as listed in Table VII to from the alprostadil cakes.

TABLE VII

Formulations of the prostaglandin solutions with various cryoprotectants

| Formulation | | Composition per vial: mg (% (w:w)) | | | |
| --- | --- | --- | --- | --- | --- |
| Code | cryoprotectant | $PGE_1$ | TBA | cryoprotectant | water |
| Pc032 | lactose monohydrate | 0.0526 (0.0070) | 7.7 (1.02) | 125 (16.67) | 617.3 (82.30) |
| Pc035 | sucrose | 0.0526 (0.0070) | 7.7 (1.02) | 125 (16.67) | 617.3 (82.30) |
| Pc036 | maltose monohydrate | 0.0526 (0.0070) | 7.7 (1.02) | 125 (16.67) | 617.3 (82.30) |

As shown in Table VIII, the alprostadil cake with maltose as cryoprotectant showed the slowest degradation rate (Pc036). On the other hand, the alprostadil cake with sucrose as cryoprotectant (Pc035) was the worst among all formulations. This indicated species of cryoprotectant could modulate the stability of $PGE_1$ in the alprostadil cake, resulting from variance of crystal structure among all formulations during lyophilization.

TABLE VIII

Stability of the obtained alprostadil cakes at 40° C. after 6 weeks

| Formulation Code | remaining $PGE_1$ (%) | $PGA_1$ (%) | water content (%) |
| --- | --- | --- | --- |
| Pc032 | 90.7 ± 1.0 $^a$ | 9.7 ± 1.1 $^a$ | 1.27 ± 0.02 $^a$ |
| Pc035 | 87.7 ± 0.9 $^b$ | 10.4 ± 0.8 $^b$ | 1.17 ± 0.05 $^b$ |
| Pc036 | 93.9 ± 0.4 $^b$ | 6.5 ± 0.3 $^b$ | 1.16 ± 0.01 $^b$ |

Results

Based on the results above, higher water content, a higher TBA content and maltose used as cryoprotectant in the prostaglandin solution were selected to improve the stability of cake.

The stability of Pc030 was further evaluated based on the result of 40° C. accelerated stability test and only 4% degradation was observed after 6 weeks incubation. Formulation Pc030 was selected for its slowest degradation rate of $PGE_1$ with lactose monohydrate. Lactose monohydrate was selected as the cryoprotectant in the following examples. Accordingly, Pc030 was selected as a suitable formulation for alprostadil cake.

TABLE IX

Candidate formulation of the alprostadil cake

| | Composition per vial: mg (% (w:w)) | | | |
| --- | --- | --- | --- | --- |
| Formulation number | $PGE_1$* | TBA | lactose monohydrate | water |
| Pc030 | 0.0526 (0.0050) | 10.8 (1.02) | 125 (11.90) | 914.2 (87.07) |

EXAMPLE 3

General Process for Preparing Liposome Solution

Liposome was composted with HSPC, cholesterol, and optional 1,2-Distearoyl-phosphatidyl ethanolamine-methyl-polyethyleneglycol conjugate (DSPE-mPEG). For forming liposome particles, the lipids were mixed and dissolved in ethanol first; and then injected into an hydration buffer, wherein the hydration buffer contains a weak acid salt, such as sodium acetate, at a pH value higher than 7. Due to amphipathic properties of lipid molecule, the liposome particles were spontaneously formed and suspended in the hydration buffer.

After liposome particles forming, the particle size was manipulated by extrusion, which liposome particles are forced to pass thorough polycarbonate membrane to obtain liposomes with an average diameter at a range of 80 nm to 180 nm. After multiple passing, the liposome particle size was down to sub-micrometer level; and the liposome particles were more stable then initial particles.

The exterior hydration buffer which liposomes suspending in were replaced by diafiltration using tangent flow filtration (TFF) with an exterior buffer to form an aqueous medium suspending the liposomes; also, some of acetate molecule inside liposomes could penetrate liposome bilayer and be removed during this process. This could generate an acetate/pH gradient across the liposome membrane; and such gradient was essential for $PGE_1$ active loading (i.e. remote loading).

Accordingly, the liposome solution for $PGE_1$ remote loading was prepared. The following experiments were designed to investigate suitable formulation parameters, process parameters, and $PGE_1$ remote loading parameters to achieve high encapsulation efficiency and sustained release of $PGE_1$.

Encapsulation efficiency was determined by a general process comprising the following steps. Liposomal and free form $PGE_1$ were separated by self-packing resin column: Firstly, a column with Toyopearl HW-55F resin in a Bio-Rad column was prepared. The sample was applied into the conditioned column and eluted by normal saline for collecting fractions of liposomal $PGE_1$, followed by eluting the column with water for collecting fractions of free form $PGE_1$. Both contents of liposomal and free form $PGE_1$ were analyzed by HPLC. The encapsulation efficiency was calculated as dividing the amount of the liposomal form $PGE_1$ with the combined amounts of the liposomal and free form $PGE_1$.

In vitro release assay was performed by a general process comprising the following steps. $PGE_1$-loaded liposome was mixed with sodium acetate buffer or human plasma (Example 6A) for triggering and accelerating release of $PGE_1$ from the liposome. The encapsulation efficiency after the release assay was determined according to the above description as the retained $PGE_1$.

EXAMPLE 4

Preparation of Liposome Solution

The liposome solutions were prepared according to the process as described in Example 3, including the descriptions of the lipid, the hydration buffer, the aqueous medium and the other parameters in the procedures of $PGE_1$ loading, such as a step of contacting the liposome solutions with lyophilized cakes, e.g., alprostadil cakes as previously described, to conduct or alprostadil in a form of solution, e.g. $PGE_1$ solution; and forming liposomal compositions. Other parameters including loading durations, drug-to-lipid ratio and final obtained encapsulation efficiency are shown in Table X.

TABLE X

Formulations of the liposome solution

| Formulation Code | Lipid composition | hydration buffer/pH | aqueous medium |
|---|---|---|---|
| PL111 | DSPC: cholesterol: DSPE-mPEG = 3:2:0.045 | 400 mM NaAc/6.5 | Double distilled water(dd$H_2$O) |
| PL112 | DSPC: cholesterol: DSPE-mPEG = 3:2:0.045 | 400 mM NaAc/8.2 | dd$H_2$O |
| PL114 | DSPC: cholesterol: DSPE-mPEG = 3:2:0.045 | 400 mM NaAc/4.0 | dd$H_2$O |
| PL115 | DSPC: cholesterol: DSPE-mPEG = 3:2:0.045 | 200 mM Ca(Ac)$_2$/7.6 | dd$H_2$O |
| PL116 | DSPC: cholesterol: DSPE-mPEG = 3:2:0.045 | 400 mM $NH_4$Ac/6.9 | dd$H_2$O |
| PL117 | DSPC: cholesterol: DSPE-mPEG = 3:2:0.045 | 400 mM KAc/7.8 | dd$H_2$O |
| PL130 | DSPC: cholesterol: DSPE-mPEG = 3:2:0.045 | 400 mM NaAc/8.2 | 20 mM histidine in 6% sucrose, pH 6.0 |
| PL141 | DSPC: cholesterol: DSPE-mPEG = 3:2:0.045 | 100 mM NaAc/8.1 | 20 mM histidine in 6% sucrose, pH 5.5 |
| PL142 | DSPC: cholesterol: DSPE-mPEG = 3:2:0.045 | 200 mM NaAc/8.3 | 20 mM histidine in 6% sucrose, pH 5.5 |
| PL143 | DSPC: cholesterol: DSPE-mPEG = 3:2:0.045 | 600 mM NaAc/8.8 | 20 mM histidine in 6% sucrose, pH 5.5 |
| PL144 | DSPC: cholesterol: DSPE-mPEG = 3:2:0.045 | 800 mM NaAc/8.9 | 20 mM histidine in 6% sucrose, pH 5.5 |
| PL153 | DSPC: cholesterol: DSPE-mPEG = 3:2:0.045 | 400 mM NaAc + 50 mM citric acid/5.07 | 20 mM histidine in 6% sucrose, pH 5.5 |
| PL154 | DSPC: cholesterol: DSPE-mPEG = 3:2:0.045 | 400 mM NaAc + 100 mM citric acid/4.70 | 20 mM histidine in 6% sucrose, pH 5.5 |
| PL155 | DSPC: cholesterol: DSPE-mPEG = 3:2:0.045 | 400 mM NaAc + 200 mM citric acid/4.19 | 20 mM histidine in 6% sucrose, pH 5.5 |
| PL156 | DSPC: cholesterol: DSPE-mPEG = 3:2:0.045 | 400 mM NaAc/8.2 | 20 mM histidine in 6% sucrose, pH 5.5 |
| PL157 | DSPC: cholesterol: DSPE-mPEG = 3:2:0.045 | 400 mM NaAc/8.2 | 20 mM histidine in 6% sucrose, pH 5.5 |
| PL158 | DSPC: cholesterol: DSPE-mPEG = 3:2:0.045 | 400 mM NaAc + citric acid/6.5 | 20 mM histidine in 6% sucrose, pH 5.5 |
| PL162 | DSPC: cholesterol: DSPE-mPEG = 3:2:0.045 | 400 mM NaAc/8.2 | 20 mM histidine in 6% sucrose, pH 5.5 |
| PL177 | HSPC: cholesterol: DSPE-mPEG = 3:2:0.045 | 400 mM NaAc + 2 mM citric acid/6.5 | 20 mM histidine in 6% sucrose, pH 5.5 |
| PL178 | HSPC: cholesterol: DSPE-mPEG = 3:2:0.045 | 400 mM NaAc + 2 mM citric acid/6.5 | 20 mM histidine in 6% sucrose, pH 5.5 |
| PL194 | HSPC: cholesterol: DSPE-mPEG = 3:2:0.045 | 400 mM NaAc + 2 mM citric acid/6.5 | 20 mM histidine in 7% lactose monohydrat, pH 5.5 |
| PL196 | HSPC: cholesterol: DSPE-mPEG = 3:2:0 | 400 mM NaAc + 2 mM citric acid/6.5 | 20 mM histidine in 7% lactose monohydrat, pH 5.5 |
| PL197 | HSPC: cholesterol: DSPE-mPEG = 3:2:0.02 | 400 mM NaAc + 2 mM citric acid/6.5 | 20 mM histidine in 7% lactose monohydrat, pH 5.5 |
| PL198 | HSPC: cholesterol: DSPE-mPEG = 3:2:0.15 | 400 mM NaAc + 2 mM citric acid/6.5 | 20 mM histidine in 7% lactose monohydrat, pH 5.5 |
| PL199 | HSPC: cholesterol: DSPE-mPEG = 3:2:0.32 | 400 mM NaAc + 2 mM citric acid/6.5 | 20 mM histidine in 7% lactose monohydrat, pH 5.5 |
| PL200 | HSPC: cholesterol: DSPE-mPEG = 3:2:0.56 | 400 mM NaAc + 2 mM citric acid/6.5 | 20 mM histidine in 7% lactose monohydrat, pH 5.5 |

NaAc represents sodium acetate; Ca(Ac)$_2$ represents calcium acetate; $NH_4$Ac represents ammonium acetate; and KAc represents potassium acetate.

EXAMPLE 5

Preparation of Liposome Solution Under Various Conditions for Improving Encapsulation Efficiency Higher encapsulation efficiency represents minimization of free form $PGE_1$. Improving encapsulation efficiency of $PGE_1$ after $PGE_1$ loading in the finally obtained liposomal composition was prioritized. The exterior and interior phase at both sides of liposome membrane were modified by changing hydration buffers and aqueous mediums to form an increased driving force for $PGE_1$ loading in this Example.

EXAMPLE 5A pH Modification of the Hydration Buffer pH value of the hydration buffer determined interior pH of liposomes. Though the interior pH could be elevated after diafiltration process by interior acetate penetrating out, the pH of the hydration buffer remained majorly contribute to the gradient across the liposome membrane for $PGE_1$ loading.

The influence of interior pH by the hydration buffer containing acetate on encapsulation efficiency was evaluated and summarized in Table XI.

TABLE XI

Formulations with the hydration buffer at various pH values

| Formulation Code | hydration buffer | | encapsulation efficiency (%) |
|---|---|---|---|
| | Buffer | pH | |
| PL114 | NaAc | 4.0 | 74.1 |
| PL111 | NaAc | 6.5 | 70.0 |
| PL112 | NaAc | 8.2 | 82.9 |

Encapsulation efficiency was assayed under identical loading condition of a drug-to-lipid ratio 20 µg:10 µmol, and 60° C. incubation for 5 minutes.

The result shows that higher buffer pH had better encapsulation efficiency. This result correlated remote loading theory: greater pH gradient with better encapsulation efficiency. The pH value of the hydration buffer was determined to be 8.2.

EXAMPLE 5B pH Modification of the Aqueous Medium pH value of the aqueous medium determined exterior pH of liposomes and also contributed to $PGE_1$ loading by influencing pH gradient across the liposome membrane. The influence of pH of the aqueous medium containing histidine at a concentration of 20 mM by adjusting pH to the levels is indicated in Table XII.

TABLE XII pH optimization of the aqueous medium

| Formulation Code | pH of the aqueous medium | encapsulation efficiency (%) |
|---|---|---|
| PL130 | 4 | 92.1 |
| | 5 | 91.8 |

TABLE XII-continued pH optimization of the aqueous medium

| Formulation Code | pH of the aqueous medium | encapsulation efficiency (%) |
|---|---|---|
| | 5.5 | 88.4 |
| | 6 | 89.1 |
| | 6.5 | 64.9 |
| | 7 | 69.1 |

Encapsulation efficiency was assayed under the following loading condition of a drug-to-lipid ratio 10 µg:5 µmol, and 20° C. incubation for 30 minutes.

Since the pH of the aqueous medium determines pH gradient across the liposome membrane, exterior pH higher than 6.0 resulted to dramatically decrease of encapsulation efficiency. The pH value of the aqueous medium was determined to be 5.5.

EXAMPLE 5C

Concentration Modification of Hydration Buffer

Concentration of the weak acid salt in the hydration buffer was another factor which might influence the encapsulation efficiency.

The influence of the concentrations of the weak acid salt as indicated in Table XIII on E.E. was evaluated and summarized in Table XIII.

TABLE XIII

Hydration buffer concentration

| Formulation Code | concentration of NaAc in the hydration buffer (mM) | encapsulation efficiency (%) |
|---|---|---|
| PL141 | 100 | 68.1 |
| PL142 | 200 | 78.0 |
| PL130 | 400 | 86.2 |
| PL143 | 600 | 86.5 |
| PL144 | 800 | 87.0 |

Encapsulation efficiency was assayed under the following loading condition: drug-to-lipid ratio 10 µg:5 µmol, and 25° C. incubation for 30 minutes.

E.E. reached plateau when concentration of sodium acetate was more than 400 mM. Higher acetate concentration did not alter encapsulation efficiency. However, a higher acetate concentration remained essential for forming acetate gradient for $PGE_1$ loading since low acetate concentration showed lower E.E.

The concentration of the weak acid salt was determined to be 400 mM sodium acetate while it generated enough gradient for $PGE_1$ loading.

Results

According to Examples 5A to 5C, the properties of the hydration buffer and the aqueous medium were determined using encapsulation approach. The hydration buffer containing 400 mM sodium acetate at pH 8.2 and the aqueous medium containing 20 mM histidine at pH 5.5 showed a desired encapsulation efficiency.

EXAMPLE 6

Preparation of Liposome Solution Under Various Conditions for Improving Sustained Release A target liposomal composition according to the present disclosure required a sustained release property to control drug release in human body. Thus, the following modifications were evaluated by not only encapsulation efficiency but also in vitro release assay to select a desired formulation.

The retained PGE percentage was determined by the method as described in the previous example.

EXAMPLE 6A

Modification of Cation in the Hydration Buffer

Cation of the weak acid salt in the hydration buffer interacted with $PGE_1$ as an anion after $PGE_1$ loading. Such interaction might slow down $PGE_1$ release. Different acetate salts were used as the weak acid salts in the hydration buffers and evaluated by encapsulation efficiency assay and in vitro release assay with human plasma.

TABLE XIV

Various cations used in the hydration buffers

| Formulation Code | hydration buffer | encapsulation efficiency (%) | retained $PGE_1$ percentage (%)* |
|---|---|---|---|
| PL112 | 400 mM NaAc | 87.6 | 13.0 |
| PL115 | 200 mM Ca(Ac)₂ | 91.1 | 0.0 |
| PL116 | 400 mM NH₄Ac | 62.0 | 12.2 |
| PL117 | 400 mM KAc | 79.6 | 34.1 |

*Using purified liposome form fraction for in-vitro release study.

Encapsulation efficiency was assayed under the following loading condition: drug-to-lipid ratio 20 µg:10 umol, 60° C. incubation for 5 minutes. In vitro release was conducted by mixing an analyte with human plasma at a ratio being 1:1, and then incubated at 37° C. for 2 hours.

Only sodium acetate and potassium acetate liposome represented both high encapsulation efficiency and retained $PGE_1$ after plasma release. Further investigations focused on these two selected formulations as shown in Table XV

TABLE XV in-vitro release results of Formulations PL112 and PL117

| Formulation Code | hydration buffer | encapsulation efficiency (%) | retained $PGE_1$ percentage (%)* |
|---|---|---|---|
| PL112 | 400 mM NaAc, pH 8.2 | 84.4 | 19.5 ± 1.8 (n = 2) |
| PL117 | 400 mM KAc, pH 7.8 | 73.2 | 28.8 ± 3.3 (n = 2) |

*Using purified liposome form fraction for in-vitro release study.

Encapsulation efficiency was assayed under the following loading condition: drug-to-lipid ratio 20 µg:10 µmol, 60° C. incubation for 5 min. In vitro release was performed by mixing an analyte with human plasma at a ratio being 1:1, and then incubated at 37° C. for 1 hour.

Although potassium acetate showed a desired release profile in plasma release assay, its initial encapsulation efficiency was much less than the group with sodium acetate as the weak acid salt. Thus, sodium acetate was selected as the weak acid salt in the hydration buffer.

EXAMPLE 6B

Addition of Citric Acid in the Hydration Buffer

According to Example 5, the hydration buffer was determined as 400 mM sodium acetate at pH 8.2. However, high pH might lead to instability of lipid. To avoid lipid instability and establishing greater acetate gradient for loading, the influence of additional citric acid at various concentrations as indicated in Table XVI were evaluated.

TABLE XVI

Hydration buffers with various citric acid concentrations

| Formulation | addition of citric acid in hydration buffer (mM) | hydration buffer pH | encapsulation efficiency (%) |
|---|---|---|---|
| PL130 | 0 | 8.4 | 87.6 |
| PL153 | 50 | 5.1 | 83.3 |
| PL154 | 100 | 4.7 | 69.2 |
| PL155 | 200 | 4.2 | 26.5 |

Encapsulation efficiency was assayed under the following loading condition: drug-to-lipid ratio 10 µg:5 umol, and 20° C. incubation for 30 minutes.

It demonstrated that additional of citric acid decreased encapsulation efficiency. However, the decease of E.E. might result from the dramatic pH decrease which was against $PGE_1$ loading.

Thus, the effect of addition of citric acid to maintain a pH of 6.5 as shown in Table XVII was further evaluated by encapsulation efficiency (E.E.) and In vitro release (IVR).

TABLE XVII

Modification of the hydration buffer with additional citric acid

| Formulation Code | hydration buffer | hydration buffer pH | encapsulation efficiency (%) | E.E. after IVR (%) |
|---|---|---|---|---|
| PL162 | 400 mM NaAc | 8.2 | 87.4 | 25.1 ± 3.3 (n = 3) |
| PL158 | 400 mM NaAc + 1.5 mM citric acid | 6.5 | 92.8 | 33.9 ± 2.0 (n = 3) |

Encapsulation efficiency was assayed under the following loading condition: drug-to-lipid ratio 10 µg:5 umol, and 20° C. incubation for 30 min. IVR was performed at a ratio of 1:1 to be mixed with 15 mM NaAc with 8.1% sucrose buffer, pH 5.5, and then incubated at 25° C. for 30 minutes.

According to the result, additional citric acid in the hydration buffer not only increased encapsulation efficiency, but also kept more $PGE_1$ inside liposome after IVR. Accordingly, the aqueous medium was thus determined to be 400 mM of sodium acetate with citric acid at a concentration ranging from 1.5 mM to 2 mM at pH 6.5.

EXAMPLE 6C

Preparation of Liposomal Composition by Modification of Drug-to-Lipid Ratio

Liposome solutions prepared according to Table X were respectively contacted with a lyophilized cake containing $PGE_1$ or a $PGE_1$ solution at a drug-to-lipid ratio as indicated below in Table XVIII (a) to form corresponding liposomal compositions. The $PGE_1$ solution was prepared by dissolving $PGE_1$ powder in an appropriate amount of ethanol to obtain a $PGE_1$ stock solution at a concentration of 5 mg/mL. For preparing liposomal composition according to the present disclosure, the liposome solution and the $PGE_1$ stock solution were diluted into 9% sucrose solution to a target concentration; and then incubated at an indicated condition for PGE$_1$ loading into liposomes.

TABLE XVIII (a)

Drug-to-lipid ratio modification

| Formulation Code | loading temperature (° C.) | loading duration (min) | drug-to-lipid ratio (PGE$_1$:lipid) |
|---|---|---|---|
| PL111 | 60° C. | 5 min | 20 µg:10 µmol$^a$ |
| PL112 | 60° C. or 20° C. | 5 min or 30 min | 20 µg:10 µmol$^a$ |
| PL114 | 60° C. | 5 min | 20 µg:10 µmol$^a$ |
| PL115 | 60° C. | 5 min | 20 µg:10 µmol$^a$ |
| PL116 | 60° C. | 5 min | 20 µg:10 µmol$^a$ |
| PL117 | 60° C. | 5 min | 20 µg:10 µmol$^a$ |
| PL130 | 20° C. or 25° C. | 10 min or 30 min | 10 µg:5 µmol$^b$ |
| PL141 | 25° C. | 30 min | 10 µg:5 µmol$^b$ |
| PL142 | 25° C. | 30 min | 10 µg:5 µmol$^b$ |
| PL143 | 25° C. | 30 min | 10 µg:5 µmol$^b$ |
| PL144 | 25° C. | 30 min | 10 µg:5 µmol$^b$ |
| PL153 | 25° C. | 30 min | 10 µg:5 µmol$^b$ |
| PL154 | 25° C. | 30 min | 10 µg:5 µmol$^b$ |
| PL155 | 25° C. | 30 min | 10 µg:5 µmol$^b$ |
| PL156 | 25° C. | 30 min | 10 µg:10 µmol$^b$ |
| PL157 | 25° C. | 30 min | 10 µg:20 µmol$^b$ |
| PL158 | 25° C. | 30 min | 10 µg:5 µmol$^b$ |
| PL162 | 25° C. | 30 min | 10 µg:5 µmol$^b$ |
| PL177 | 25° C. | 10 min | 10 µg:10 µmol$^b$ |
| PL178 | 25° C. | 10 min | 10 µg:20 µmol$^b$ |
| PL194 | 25° C. | 10 min | 10 µg:10 µmol$^b$ |
| PL196 | 25° C. | 10 min | 10 µg:10 µmol$^b$ |
| PL197 | 25° C. | 10 min | 10 µg:10 µmol$^b$ |
| PL198 | 25° C. | 10 min | 10 µg:10 µmol$^b$ |
| PL199 | 25° C. | 10 min | 10 µg:10 µmol$^b$ |
| PL200 | 25° C. | 10 min | 10 µg:10 µmol$^b$ |

After PGE$_1$ loading at a drug-to-lipid ratio ranging from 5 to 20 µg to 10 µmol at a condition of at a incubation temperature ranging from 20 to 60° C. for 5 to 30 minutes, the encapsulation efficiency of PGE$_1$ in the obtained liposomal composition by mixing the liposome solutions with the alprostadil cake were evaluated respectively, ranging from about 70% to 97.1 ± 1.2%.
$^a$Liposome solution was loaded with a PGE$_1$ solution.
$^b$Liposome solution was loaded with a lyophilized cake containing PGE$_1$.

In initial formulation, the drug-to-lipid ratio was predetermined to be 10 µg:5 µmol. To further increase the encapsulation efficiency and sustain release property of liposomes, drug-to-lipid ratio in PGE$_1$ loading was modified and results of E.E of PL130, PL156 and PL 157 were summarized as in Table XVIII (b).

TABLE XVIII (b)

Drug-to-lipid ratio modification

| Formulation | drug-to-lipid ratio | encapsulation efficiency (%) |
|---|---|---|
| PL130 | 10 µg:5 µmol | 87.6 |
| PL156 | 10 µg:10 µmol | 91.9 |
| PL157 | 10 µg:20 µmol | 97.1 ± 1.2 (n = 4) |

Encapsulation efficiency was assayed under the following loading condition: 25° C. incubation for 30 minutes.

Lower drug-to-lipid ratio increased encapsulation efficiency. Afterwards, further tested were the drug-to-lipid ratios at 10 µg:10 µmol and 10 µg:20 µmol liposomes at a condition of incubation at 25° C. for 10 minutes.

TABLE XIX

Lower drug-to-lipid ratio liposomes

| Formulation | drug-to-lipid ratio | encapsulation efficiency (%) (n = 3) | E.E. after IVR (%) (n = 3) |
|---|---|---|---|
| PL177 | 10 µg:10 µmol | 92.9 ± 1.7 | 36.62 ± 1.35 |
| PL178 | 10 µg:20 µmol | 95.6 ± 1.7 | 48.83 ± 3.02 |

Encapsulation efficiency was assayed under the following loading condition: 25° C. incubation for 10 minutes. IVR was performed at a ratio of 1:1 to mix with 15 mM NaAc with 8.1% sucrose buffer, pH 5.5, and then incubated at 25° C. for 15 minutes.

Lowering drug-to-lipid ratio slightly increased both encapsulation efficiency and E.E. after IVR. However, drug-to-lipid ratio as 10 µg:20 µmol was so low. Therefore, the drug to lipid ratio of 10 µg:10 µmol was determined.

EXAMPLE 7

Modulation of mPEG Content

The amounts of phosphocholine and cholesterol were fixed at a molar ratio being 3:2 because this type of composition gives greatest condense arrangement of lipids. As for DSPE-mPEG, which generated surface negative charge for avoiding liposome clearance in human body or liposome aggregation, altered PGE$_1$ loading and IVR as shown in Table XX.

TABLE XX

Modulation of mPEG content

| Formulation | mPEG content (mol %) | encapsulation efficiency (%) | E.E. after IVR (%) |
|---|---|---|---|
| PL196 | 0 | 76.6 | 52.6 |
| PL197 | 0.4 | 83.5 | 49.9 |
| PL194 | 0.9 | 98.6 | 59.1 |
| PL198 | 3 | 95.5 | 58.6 |
| PL199 | 6 | 85.4 | 36.9 |
| PL200 | 10 | 86.7 | 40.9 |

Encapsulation efficiency was assayed under the following loading condition: drug-to-lipid ratio 10 µg:10 µmol, and 25° C. incubation for 10 minutes. For IVR assay, after 1 hour of PGE$_1$ loading (for equilibrium loading), the obtained liposome solution was at a ratio 9:1 (v/v) mixed with 75 mM sodium acetate releasing buffer, and incubated at 37° C. for 15 minutes.

Figure 2:
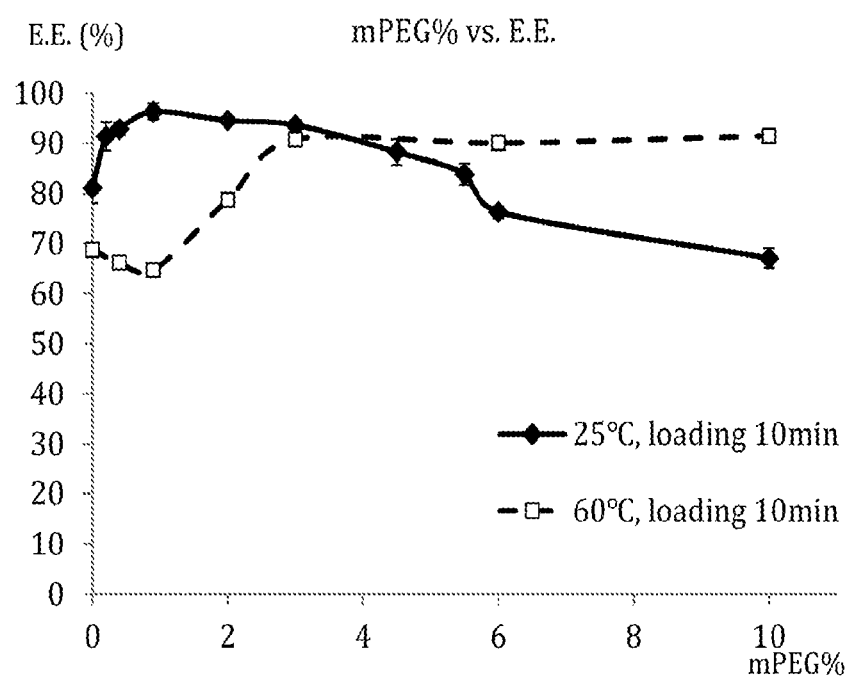
FIG. 2 illustrating a diagram of encapsulation efficiency versus a titration of polyethylene glycol-derived lipid in liposomal composition obtained according to Example 7.

As shown in Table XX and FIG. 2, DSPE-mPEG molar ratio between 0.9% and 3% (i.e. HSPC:cholesterol:DSPE-mPEG=3:2:0.045 to 3:2:0.15) shown highest encapsulation efficiency under incubation for 10 minutes. Further, the amount of the retained PGE$_1$ ranked high among these formulations after IVR assay. The final lipid composition was determined to contain lipid at a ratio of HSPC:cholesterol:DSPE-mPEG=3:2:0.045.

Results

According to Examples 6A to 6C and 7, the formulation of liposome solution was modified as a lipid composition with HSPC:cholesterol:DSPE-mPEG=3:2:0.045; the hydration buffer containing 400 mM of sodium acetate and 2 mM of citric acid at pH 6.5; and the drug-to-lipid ratio of 10 µg:10 µmol as shown in Table XXI.

TABLE XXI

Composition of PL194 formulation

| Formulation code | lipid molar ratio | | | hydration buffer | | aqueous medium | |
|---|---|---|---|---|---|---|---|
| | HSPC | Cholesterol | DSPE-mPEG | Salt | pH | Salt | pH |
| PL194 | 3 | 2 | 0.045 | 400 mM NaAc + 2 mM citric acid | 6.5 | 20 mM histidine + 7% Lactose monohydrate | 5.5 |

Such formulation showed high $PGE_1$ encapsulation efficiency (about 90%) after loading at ambient temperature within a short period of time (10 minutes); and retained more $PGE_1$ than other formulations in IVR assay.

EXAMPLE 8

In Vivo Evaluation of Efficacy of $PGE_1$ Formulations by Using Blood Flow Analysis The efficacy of the liposomal compositions PL157 and PL194 was compared to free-drug ($PEG_1$-CD) treated animals by blood flow study as described below.

Blood Flow Study

Wistar rats were anesthetized by isoflurane and kept body temperature on a heating pad (36.5° C.). When the animals were deeply anesthetized, cutaneous microvascular blood flow of toruli digitales on the digitus quintus of right caudal paw was recorded by Laser Doppler Flowmetry (MoorVMS LDF1, Moor Instruments Ltd) 5 minutes before intravenous administration of 3 ug/kg of $PGE_1$-CD or the liposomal compositions and then continuously recorded for another 20 minutes to monitor the response after dose. Raw data of flux value was recorded by software of moorVNS-PCV2.0 and exported to Excel file (Microsoft software) for data processing.

The blood flow data was normalized and plotted on graphs, and the parameters $BF_0$, $BF_{max}$ and AUC % were calculated, wherein $BF_0$ represents mean blood flow of baseline; $BF_{max}$ represents maximum blood flow post dose; AUC % represents the percentage of area under the curve from 0 to 20 min of blood flow compared to baseline AUC.

Results

As shown in Table XXII and Table XXIII, both PL194 and PL157 caused higher $BF_{max}/BF_0$ and larger AUC ratio in comparison to $PGE_1$-CD.

PL194 caused slightly lower $BF_{max}/BF_0$ ratio and smaller AUC ratio compared to PL157.

TABLE XXII

Study 1

| Formulation | Dose (µg/kg) | No. of animal | $BF_0$ (mL/min/100 g) | $BF_{max}$ (mL/min/100 g) | $BF_{max}/BF_0$ | AUC % |
|---|---|---|---|---|---|---|
| PL157 | 3 | 5MX3 | 10.5 ± 0.5 | 18.7 ± 1.7* | 1.8 ± 0.2[#] | 142.4 ± 9.9[#] |
| $PGE_1$-CD | 3 | | 11.7 ± 0.6 | 15.7 ± 0.8* | 1.3 ± 0.0 | 117.2 ± 3.5 |

Mean ± S.E.
*$p < 0.05$ as compared to $BF_0$;
[#]$p < 0.05$ as compared to $PGE_1$-CD

TABLE XXIII

Study 2

| Formulation | Dose (µg/kg) | No. of animal | $BF_0$ (mL/min/100 g) | $BF_{max}$ (mL/min/100 g) | $BF_{max}/BF_0$ | AUC % |
|---|---|---|---|---|---|---|
| PL194 | 3 | 7M | 15.6 ± 1.4 | 25.2 ± 4.2* | 1.6 ± 0.1[#] | 137.1 ± 8.2[#] |
| $PGE_1$-CD | 3 | | 16.3 ± 1.3 | 22.6 ± 5.9* | 1.4 ± 0.0 | 117.2 ± 2.0 |

Mean ± S.E.
*$p < 0.05$ as compared to $BF_0$;
[#]$p < 0.05$ as compared to $PGE_1$-CD The formulations of both the alprostadil cake and liposome solution were investigated as above. The formulation processed desired properties reflected by stability test and animal study. For the alprostadil cake, Formulation Pc030 or Pc036, showed the preferable stability among the others. For the liposome solution, Formulation PL194, showed highly encapsulation efficiency within a short loading duration at ambient temperature condition; also, the retained $PGE_1$ was more than other formulations in IVR study.

As results of blood flow shown, the liposomal composition according to the present disclosure indeed acquires an improved efficacy in comparison to the conventional prostaglandin composition.

Even though numerous characteristics and advantages of the present disclosure have been set forth in the foregoing description, together with details of the structure and features of the disclosure, the disclosure is illustrative only. Changes may be made in the details, especially in matters of shape, size, and arrangement of parts within the principles of the disclosure to the full extent indicated by the broad general meaning of the terms in which the appended claims are expressed.

This application claims the benefit under 35 U.S.C. § 119(e) to U.S. Provisional Application Nos. 62/372,096, filed Aug. 8, 2016 and 62/375,698, filed Aug. 16, 2016, which applications are hereby incorporated by reference in their entirety.

What is claimed is:

1. A delivery vehicle, comprising a liposome in an aqueous medium and a mild acidic agent encapsulated within the liposome, wherein the liposome has an aqueous interior space with a combination of a weak acid salt and a polyprotic acid therein, and the aqueous interior space is separated from the aqueous medium by a membrane of the liposome;
   wherein the membrane comprises a lipid mixture containing one or more lipids and a polyethylene glycol-derived lipid, wherein the polyethylene glycol-derived lipid is at a molar percentage of 0.5 to 3% based on the total amount of the lipid mixture;
   the weak acid salt is sodium acetate or potassium acetate;
   the polyprotic acid is selected from the group consisting of citric acid, succinic acid, tartaric acid and a combination thereof;
   wherein the concentration of the weak acid salt is between 100 mM and 800 mM;
   wherein the concentration of the polyprotic acid is not greater than 50 mM; and
   the combination of the weak acid salt and the polyprotic acid is at a molar ratio of weak acid salt to polyprotic acid ranging from 8:1 to 200:1.

2. The delivery vehicle according to claim 1, wherein the concentration of the weak acid salt is at a range between 200 mM and 800 mM.

3. The delivery vehicle according to claim 1, wherein the concentration of the polyprotic acid is at a range selected from the group consisting of: less than 10 mM, between 0.01 mM and 5 mM, between 0.1 mM and 3 mM, and between 1.5 mM and 2.5 mM.

4. The delivery vehicle according to claim 1, wherein the polyethylene glycol-derived lipid is at a molar percentage ranging from 0.5% to 1%.

5. The delivery vehicle according to claim 1, wherein the aqueous medium has a pH value less than 6.5.

6. A liposomal composition comprising a liposome in an aqueous medium, wherein the liposome has an aqueous interior space with a combination of a weak acid salt and a polyprotic acid therein at a molar ratio of weak acid salt to polyprotic acid ranging from 8:1 to 200:1, and the aqueous interior space is separated from the aqueous medium by a membrane of the liposome; and
   a mild acidic agent encapsulated within the liposome;
   wherein the concentration of the weak acid salt is between 100 mM and 800 mM;
   wherein the concentration of the polyprotic acid is not greater than 50 mM; and
   wherein the membrane comprises a lipid mixture containing one or more lipids and a polyethylene glycol-derived lipid, wherein the polyethylene glycol-derived lipid is at a molar percentage of 0.5 to 3% based on the total amount of the lipid mixture.

7. The liposomal composition according to claim 6, wherein the concentration of the weak acid salt is at a range between 200 mM and 800 mM.

8. The liposomal composition according to claim 6, wherein the concentration of the polyprotic acid is at a range between 0.01 mM and 5 mM.

9. The liposomal composition according to claim 6, wherein the molar ratio of the mild acidic agent to the total lipids of the liposomal composition is at a range of at least 0.001:1.

10. The liposome composition according to claim 9, wherein the molar ratio of the mild acidic agent to the amount of total lipids of the liposomal composition is at a range from 0.001:1 to 0.05:1.

11. The liposomal composition according to claim 6, wherein the mild acidic agent is arachidonic acid metabolite.

12. The liposomal composition according to claim 6, wherein the mild acidic agent is a prostaglandin.

13. The liposome composition according to claim 6, wherein the weak acid salt is sodium acetate or potassium acetate.

14. The liposome composition according to claim 6, wherein the polyprotic acid is selected from the group consisting of citric acid, succinic acid, tartaric acid and a combination thereof.

15. A liposomal composition comprising:
    a liposome having a membrane comprised of one or more lipids and a polyethylene glycol-derived lipid, wherein the polyethylene glycol-derived lipid is at a molar percentage of 0.5 to 3%; and a combination of an acetate salt and a citric acid at a molar ratio of acetate salt to citric acid ranging from 8:1 to 200:1 encapsulated within the liposome;
    wherein the concentration of the acetate salt is between 100 mM and 800 mM;
    wherein the concentration of the citric acid is not greater than 50 mM; and
    prostaglandin entrapped by the combination of the acetate salt and the citric acid encapsulated within the liposome.

* * * * *